(12) United States Patent
Ciribolla

(10) Patent No.: US 6,461,664 B1
(45) Date of Patent: Oct. 8, 2002

(54) CHELATED FEED ADDITIVE AND METHOD OF PREPARATION

(75) Inventor: Antonio Ciribolla, Reggio Emilia (IT)

(73) Assignee: Agristudio S. r. L., Reggio Emilia (IT)

( * ) Notice: Subject to any disclaimer, the term of this patent is extended or adjusted under 35 U.S.C. 154(b) by 0 days.

(21) Appl. No.: 09/807,958

(22) PCT Filed: Jul. 19, 1999

(86) PCT No.: PCT/IT99/00225

§ 371 (c)(1),
(2), (4) Date: Apr. 26, 2001

(87) PCT Pub. No.: WO00/53032

PCT Pub. Date: Sep. 14, 2000

(30) Foreign Application Priority Data

Mar. 5, 1999 (IT) .......................................... RE99A0028

(51) Int. Cl.[7] ........................... A23K 1/16; A23K 1/175
(52) U.S. Cl. ........................................ 426/656; 426/807
(58) Field of Search .................................. 426/656, 807

(56) References Cited

U.S. PATENT DOCUMENTS 3,175,000 A * 3/1965 Gielken et al. ............. 260/535
4,419,198 A * 12/1983 Breda et al. ................. 204/180
4,579,962 A * 4/1986 Takano ........................ 556/131
4,855,495 A * 8/1989 Takano et al. .............. 562/581

FOREIGN PATENT DOCUMENTS

| EP | 0 049 057 A1 | * | 4/1982 |
| GB | 2044755 | * | 3/1979 |
| JP | 11 0 75885 | * | 3/1999 |
| WO | WO96/36598 | * | 11/1996 |

OTHER PUBLICATIONS

Patent Abstracts of Japan, vol. 1999, No. 08, Jun. 30, 1999 & JP 11 075885 A.*

* cited by examiner

Primary Examiner—Chhaya D. Sayala
(74) Attorney, Agent, or Firm—Arent Fox Kintner Plotkin & Kahn

(57) ABSTRACT

Feed additive for agro-zootechnical use, in particular for alimentary use in the zootechnical sector, consisting of a chelate obtained by the reaction of methionine hydroxy analogue with the carbonate of a bivalent metal. The reaction is free from undesirable by-products, and the product is stable and effective in improving the main growth factors of the animal.

13 Claims, No Drawings

CHELATED FEED ADDITIVE AND METHOD OF PREPARATION

TECHNICAL FIELD

The present invention relates to a chelated additive for agro-zootechnical use in the broad sense, and in particular for alimentary use in the zootechnical sector, and the associated method for obtaining said additive. A chelate is a compound which is obtained from an organic molecule (in the case in question an amino acid or a peptide chain) and a metal ion by means of strong co-ordination bonds.

BACKGROUND ART

These compounds are widely used both in the agronomic field and in the zootechnical field since their usefulness is derived from the biological action of the metal involved, which acts as activator in a great number of enzymatic reactions and as regulator in various metabolic functions in all living organisms.

The presence of the bond with an amino acid material favours the absorption, availability and use of the metal since it is transported by the organic component to all areas of the organism.

Within the zootechnical sector in particular, these compounds are used in various breeding or rearing sectors to increase and strengthen the normal metabolic and functional activities of organs and apparatuses, with considerable positive effects on the capacities for productive growth of the animals.

The chelates currently present on the international market may be classified in various categories. The best known category is that which groups together the metal ions which form a complex with specific single amino acids. They are well definable compounds in terms of chemical composition and are easily assimilated and available for the organism.

A second category is composed of micronutrients which form a complex with single amino acids which, even though not well definable in this case, possess characteristics similar to those of the preceding group.

During production of these compounds, it was noted, moreover, that some soluble metal salts are difficult to chelate or leave undesirable residual products such as, for example, phosphoric acid or hydrochloric acid.

A third category contains metal ions which form a complex with several amino acids, preferably a maximum of three up to a molecular weight of 800 daltons.

The greater size of the molecule, however, results in a weaker bonding strength and greater difficulty of absorption.

A further category is composed of proteins which are obtained from the combination of a metal ion with a peptide chain. These compounds, the amino acid composition of which is not known, may interact with other substances contained in the food and therefore be of limited availability for the animal.

Finally, there are metals which form a complex with polysaccharide chains, in which the organic component has little effect on the real nutritional requirements of the animal and the metals are combined with organic acids, which are very soluble, but may easily dissociate in the intestines, with adverse effects in terms of lowering of the intestinal pH.

DISCLOSURE OF THE INVENTION

The object of the present invention is to obtain an additive for agro-zootechnical use and in particular for alimentary use in the zootechnical sector, in which a metal, which may also be classified among the micronutrients, is bonded to an amino acid via a strong chelating bond, this product being not only effective, but also stable and easily reproducible, and free from undesirable reaction by-products.

The objects are achieved by using a methionine in solution with an acid function (methionine hydroxy analogue) and reacting it with a carbonate of a bivalent metal, starting the reaction of the two components in particular with less methionine, relative to the carbonate.

Experiments carried out using the product thus obtained on dairy cattle have shown that the invention has positive and important effects on the animals.

Two groups of animals were prepared, one test group supplied with ordinary metal salts, and one experimental group supplied with the same quantity of chelated metal ions, but with the methionine hydroxy analogue according to the invention, in doses of about 10 g per head of cattle per day.

At the end of the test, the following results were observed in the treated group: a significant improvement in all the reproductive factors (fertility, succesful pregnancies, more rapid return to heat and improved ovary activity) and reduction in infections of the uterus and cases of mastitis following an improvement in the immune state of the animal, which allowed the latter to withstand effectively all the problems of an infective and metabolic nature which are typical of the postnatal period. Similar experiments were carried out on some meat cattle stock, distinguishing a test group from an analysis group and supplying the said groups with identical quantities of metal ions, one in salt form and the other in chelated form for about three months, in doses of about 10 g per head of cattle per day.

In this latter test, too, surprisingly a greater resistance to environmental stresses on the part of the animals, in the form of improved productive performances (growth and conversion factors, body growth), was noted. A reduction in podalic pathologies (laminitis, ulcers and interdigital dermatitis) was also detected.

The invention will emerge more clearly from the description of a working example illustrated below.

DETAILED DESCRIPTION OF THE PREFERRED EMBODIMENTS

EXAMPLE No. 1

The structural formula of a chelate according to the invention, obtained from the reaction of a methionine hydroxy analogue with the carbonate of a bivalent metal, in the presence of water, is shown:

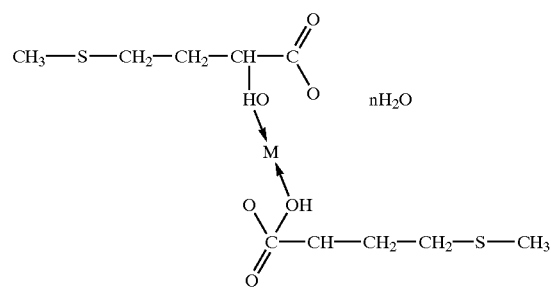

and in short $(CH_3SCH_2CH_2CHOHCOO)_2M \cdot nH_2O$ where M may be a bivalent metal and is in general $Zn^{2+}$, $Cu^{2+}$, $Co^{2+}$, $Mn^{2+}$, $Ca^{2+}$, $Fe^{2+}$ or $Mg^{2+}$.

Said compound was prepared using in particular zinc carbonate; it is obtained from the reaction of two molecules of methionine hydroxy analogue + one of $ZnCO$.:
$2CH_3SCH_2CH_2CHOHCOOH+ZnCO \rightarrow (CH_3SCH_2CH_2CHOHCO)_2Zn+H_2O+CO_2$ where, since the reaction takes place in an aqueous solution, water of crystallization may be present in the dried chelate.

The reaction takes place in the presence of a small amount of demineralized water, at temperatures of between 25° C. and 35° C. and at ambient pressure, with the evolution of $CO_2$.

Although the reaction is slightly exothermic, slight heating up to 40° C. may be appropriate in order to accelerate the process and facilitate the evaporation of the excess water.

In the case described, the dried chelate is in the form of a white powder, with a melting point of about 248° C. and a solubility in water of about 20 g/l at ambient temperature.

The infrared vibrational absorption spectrum indicates that the chelating process has taken place: in fact, the spectrum exhibits a series of characteristic bands, in accordance with the structure described above. The strongest bands are indicated below (values in $cm^{-2}$): 3219 (OH stretching); 2918 (CH stretching); 1591 (COO asymmetrical stretching); 1422 (COO symmetrical stretching+OH bending); 1307 (CH bending); 1088 (C-OH stretching).

The method of preparation of the product is as follows: One mole of zinc carbonate is poured, together with demineralized water slightly heated to about 35° C., in a sufficient quantity to dissolve the zinc carbonate, into a mixer or a reactor provided with a mixer.

The optimum temperature range is in any case between 20° C. and 40° C.

The mixer is turned on and the methionine hydroxy analogue is added slowly so as to avoid the undesirable effects of a strong evolution of $CO_2$ and overheating of the mixture. The stoichiometric ratio is two moles of methionine hydroxy analogue to one mole of zinc carbonate; said ratio being reached slowly by means of successive additions of methionine while mixing is continued for a duration of between one and two hours so as to favour the generation of $CO_2$ and evaporation of the excess water.

During the entire reaction, the methionine/metal carbonate stoichiometric ratio is less than the theoretical ratio, approaching the theoretical value asymptotically at the end of the reaction.

Once the product has reached a paste-like consistency, drying may be performed by means of the normal drying processes which are known today, or by adding adsorbent products (silica, corn-cob flour).

In this way a stable product, which is pure in that it is devoid of reaction by-products, is obtained.

Moreover this modified amino acid offers considerable advantages over other common amino acids in that:

it can be more easily assimilated in the duodenum and is less susceptible to degradation of the ruminal bacterial flora;

it may be rapidly detected in the blood and is therefore available for production;

it can be mixed uniformly without the risk of compaction;

it is compatible with vitamins, fats and minerals present in the diet;

it increases the efficiency of anti-mould products owing to its acid characteristics;

absorption thereof in the intestines does not require energy which is dissipated in the form of a dynamic specific action.

The chelate obtained was prepared using simple apparatuses already present in any normal additive-manufacturing industry.

Finally the costs for these operations are very low. Possible variants:

The possible variants are obtained by simply exchanging the bivalent metal (cuprous ion, zinc, manganous ion, cobalt, ferrous ion) chelated in each case with the organic molecule.

For example, if, for the sake of brevity, HMetOH designates the methionine hydroxy analogue where H is the exchangeable acid, the solid products which can be obtained by the process illustrated above may be indicated by $M(MetOH)_2 \cdot nH_2O$ where M is the bivalent metal cation of a carbonate.

When M is $Co^{2+}$, a pink powder with a melting point >310° C. is obtained.

When M is $Mn^{2+}$, a light brown powder with a melting point >310° C. is obtained.

When M is $Cu^{2+}$, a light green powder with a melting point of 202° C. is obtained.

Each metal ion has particular characteristics with regard to given enzymatic and metabolic systems of the animal or the plant to which it is administered, whereby the advantages of administering it in the form of a chelate bonded to a methionine hydroxy analogue remain unaffected.

Illustrated with regard to applications in the zootechnical sector, the additive according to the invention may also find widespread application in the agronomic sector, where the presence of the bond between the bivalent metal and an amino acid material favours the absorption, availability and use of the metal since it is transported by the organic component to the vegetable tissue.

What is claimed is:

1. An additive for agro-zootechnical alimentary use in the zootechnical sector, consisting of a chelate produced by the combination of an organic molecule with a metal, characterized in that it is represented by the formula $(CH_3SCH_2CH_2CHOHCOO)_2M \cdot nH_2O$ in which the organic part consists of two anions derived from methionine-hydroxy-analogue, the inorganic part consisting of a bivalent metal M selected from the group consisting of $Zn^{2+}$, $C^{2+}$, $C^{2+}$, $Mn^{2+}$, $Ca^{2+}$ and $Fe^{2+}$, M being derived from a carbonate salt $MCO_3$ and n is a number of water molecules.

2. The additive according to claim 1, wherein the chelate is represented by the formula $(CH_3SCH_2CH_2CHOHCOO)_2 Zn \cdot nH_2O$.

3. The additive according to claim 1, wherein n is 2 having the following characteristics: white powder, with a melting point of about 248° C., solubility in water of about 20 g/l at ambient temperature; and infrared vibrational absorption spectrum having a series of characteristic bands (values in $cm^{-1}$): 3219 (OH stretching); 2918 (CH stretching); 1591 (COO asymmetrical stretching); 1422 (COO symmetrical stretching+OH bending); 1307n (CH bending); 1088 (C-OH stretching).

4. The additive according to claim 1, wherein the chelate is represented by the formula $(CH_3SCH_2CH_2CHOHCOO)_2 Cu \cdot nH_2O$.

5. The additive according to claim 1, wherein the chelate is represented by the formula $(CH_3SCH_2CH_2CHOHCOO)_2 Co \cdot nH_2O$.

6. The additive according to claim 1, wherein the chelate is represented by the formula $(CH_3SCH_2CH_2CHOHCOO)_2 Mn \cdot nH_2O$.

7. The additive according to claim 1, wherein the chelate is represented by the formula $(CH_3SCH_2CH_2CHOHCOO)_2 Ca \cdot nH_2O$.

8. The additive according to claim 1, wherein the chelate is represented by the formula $(CH_3SCH_2CH_2CHOHCOO)_2 Fe \cdot nH_2O$.

9. A method for preparing an additive consisting of the chelate according to claim 1, characterized in that said method consists of the following phases:
   a) dissolving a carbonate salt $MCO_3$ in the presence of water for obtaining a solution;
   b) mixing the solution;
   c) adding slowly and continuously a methionine-hydroxy-analogue to the solution, until the stoichiometric ratio of two moles of methionine-hydroxy-analogue to one mole of $MCO_3$ is reached; and
   d) drying.

10. The method according to claim 9, wherein the carbonate salt $MCO_3$ is dissolved into a mixer.

11. The method according to claim 10, wherein the carbonate salt $MCO_3$ is dissolved at the temperature range from 20° C. to 40° C.

12. The method according to claim 9, wherein said stoichiometric ratio is reached slowly by means of successive additions of methionine-hydroxy-analogue while mixing is continued so as to favor the generation of $CO_2$ and evaporation of the excess of water for obtaining the chelate having formula $(CH_3SCH_2CH_2CHOHCOO)_2M \cdot nH_2O$ at the end of the reaction.

13. The method according to claim 12, wherein the additions of methionine-hydroxy-analogue while mixing is continued for a duration of between one and two hours.

* * * * *